United States Patent [19]

Herbin et al.

[11] Patent Number: 4,852,182

[45] Date of Patent: Jul. 25, 1989

[54] PROCESS FOR OBTAINING IMAGES OF GEOLOGICAL SAMPLES WITH A VIEW TO THEIR OPTICAL ANALYSIS AND A DEVICE FOR ITS IMPLEMENTATION

[75] Inventors: Jean-Paul Herbin, Nanterre; Claude Lallemand, Paris; Georges Gess, Montpellier, all of France

[73] Assignee: Institut Francais du Petrole, Rueil-Malmaison, France

[21] Appl. No.: 731,018

[22] Filed: May 6, 1985

[30] Foreign Application Priority Data

May 11, 1984 [FR] France ................................ 84 07284

[51] Int. Cl.⁴ .............................................. G06K 9/00
[52] U.S. Cl. .......................................... 382/1; 73/153; 250/253; 250/255
[58] Field of Search ...................... 356/326, 328, 445, , 356/308, 36; 250/359.1, 253, 226, 255, 363 S; 382/1, 17, 34; 358/206; 73/153, 151

[56] References Cited

U.S. PATENT DOCUMENTS

| | | | |
|---|---|---|---|
| 3,572,945 | 3/1971 | Thompson | 250/226 |
| 3,869,212 | 3/1975 | Burcher et al. | 356/308 |
| 3,908,078 | 9/1975 | Auerbach | 382/34 |
| 4,120,045 | 10/1978 | Moellgaard | 382/50 |
| 4,146,332 | 3/1979 | Moore | 356/308 |
| 4,149,804 | 4/1979 | Chew, III | 356/36 |
| 4,281,249 | 7/1981 | Lapidus | 250/363 S |
| 4,464,786 | 8/1984 | Nishito | 382/34 |
| 4,591,718 | 5/1986 | Amer | 250/339 |
| 4,616,134 | 10/1986 | Pruett | 250/255 |
| 4,623,792 | 11/1986 | Böhne | 250/255 |
| 4,829,218 | 8/1974 | Alyanak | 356/326 |

*Primary Examiner*—Leo H. Boudreau
*Assistant Examiner*—Joseph Mancuso
*Attorney, Agent, or Firm*—Antonelli, Terry & Wands

[57] ABSTRACT

A process and device for optical analysis of a geological core taken out from penetrated underground formations. A core is moved step by step with respect to an opto-electronic system which enables successive images of parallel lines of a surface of the core to be obtained by the opto-electronic system with the line images being converted to electric digital signals. The electric digital signals are recorded and data of the recorded signals of images of the core is compared with data from signals of line images of other core surfaces previously recorded, thereby enabling geological characteristics of the penetrated underground formations to be more easily classified.

15 Claims, 1 Drawing Sheet

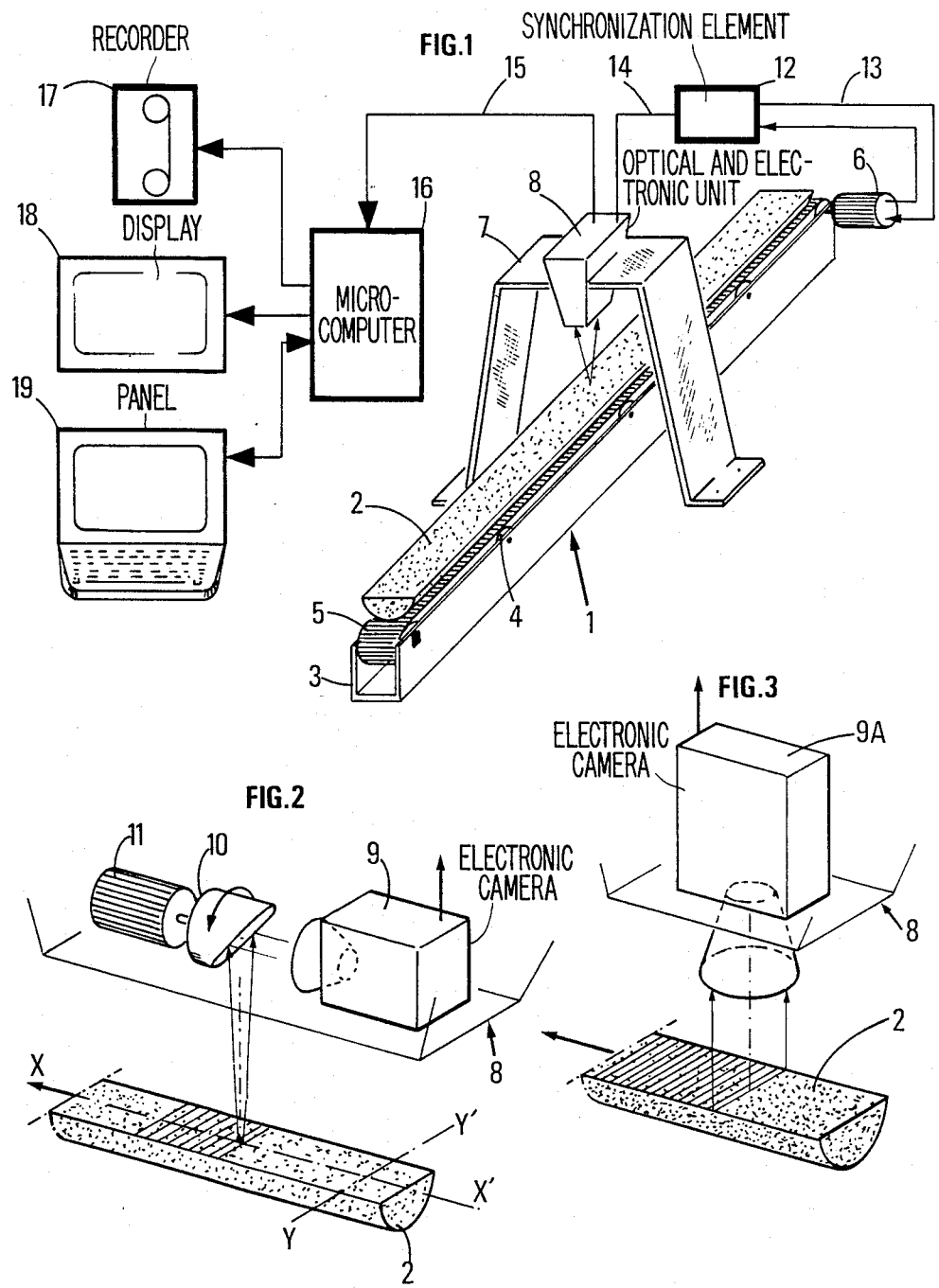

PROCESS FOR OBTAINING IMAGES OF GEOLOGICAL SAMPLES WITH A VIEW TO THEIR OPTICAL ANALYSIS AND A DEVICE FOR ITS IMPLEMENTATION

BACKGROUND OF THE INVENTION

The invention aims to provide a process enabling images to be obtained of geological samples with a view to their optical analysis, together with a device for its implementation.

These samples, which may be of small dimensions, appear in the form of cores taken at various depth levels in boreholes. Once brought to the surface, the cores are prepared for a visual examination, the observations of which form teh subject of a descriptive report. This examination report, based on interpretations and codifications using conventional sedimentology symbols and charts, seeks to define, for example, the form, structure, colour and minerological composition of each sample.

The cores are then quickly stored in conditions ensuring their sound preservation, which often limits the possibilities of direct visual comparison between samples made on a given site.

The comparisonn of these samples and a fortiori the research conducted subsequently, which involves comparative analyses of samples obtained on different sites, may often only be carried out, for practical reasons, on the single basis of descriptive reports, in other words on data already interpreted. The analysis work of geologists is consequently slowed down and rendered more difficult.

SUMMARY OF THE INVENTION

The process according to the invention enables the drawbacks linked to previous interpretation methods to be avoided.

It is characterized in that it includes the sequential recording, on a storage or recording medium, of electrical signals translating the images of parallel lines on the surface of each sample, the images of said lines being successively formed by the relative movement of samples in relation to the recording system. The recorded signals correspond, for example, to images obtained by a selection of at least on spectral band in the radiations received from the said object. The signals obtained are preferably digitalised whilst being recorded.

The process according to the invention is useful in that the recorded signals can be restored at any moment on an appropriate support, e.g. television screen, photosensitive film or paper, in order to be directly observed or compared with others and, in addition, lend themselves to all sorts of computer-aided processings enabling the physical characteristics of samples to deduced objectively without recourse to visual interpretations.

BRIEF DESCRIPTION OF THE DRAWINGS

It will be seen more clearly in the description which follows of the preferred realization modes of the process and its implementation device and by referring to the accompanying drawings on which :

FIG. 1 diagramatically represents the device enabling a geological sample to be moved, where this involves obtaining images, in relation to a recording system ;

FIG. 2 represents a realization mode of the recording system where a revolving mirror is used to direct the images of the points of each sample line successively towards a camera, and FIG. 3 represents a second realization mode of the recording system where the images of the object are obtained and recorded line by line.

DETAILED DISCUSSION OF THE DRAWINGS

By referring to FIG. 1, it can be seen that the device includes, for example, a mobile table 1 with dimensions adapted to hose of the object 2 to be recorded. When the object is a geological core, the table consists, for example, of a frame several meters long adapted to support the axes of rollers 4 on which a mat 5 is laid. A drive motor 6 of the step--by-step type is used to drive on the of rollers in such a way as it results in a discontinuous displacement of the mat. Above the mobile table a portico 7 is arranged, to which is fixed a box 8 containing an optical and electronic unit for transforming into recordable signals the images of the object's various parts successively carried into its field by the discontinuous movement of the mat.

This optical and electronic unit includes, for example (Fig.2), an electronic camera 9 and optical means for directing onto the lens of othe camera the light successively originating from all the surface points of the object placed on the table 1. These means include, for example, a revolving mirror 10 rotated by a motor 11. The mirror rotation axis and the optical axis of the camera are disposed parallel to the displacement direction X'X of the object. In this way, the surface of the object is successively explored following transversal lines parallel to the orthogonal axis Y'Y, the images of the various points of each line being successively recorded by the camera 9. Mirror rotation is controlled in such a way that scanning of the points of each line is carried out in a time interval when the mat 5 is stationary.

This optical and electronic unit may also include (FIG. 3) a camera 9A of a known type suitable for recording the images of surface lines of the object successively formed on its lens. The line images are received by the terminals of adjacent photosensitive sensors. The elelctrical signals generated by these sensors in response to illumination are successively read, the image of each line corresponding to a sequence of signals. The sensors are, for example, of the charge coupled device type (CCD) or made up of photodiodes.

The device also includes a synchronization element 12 connected firstly to a motor 6 by a cable 13 and secondly to the optical and electronic unit contained in the box 8 by a cable 14. The synchronization element 12 is provided with an internalclock and a counter and, in response to he pulses produced by the clock, it generates successive control signals which are applied to he motor 6. The latter then turns from an angular increment which has the effect of displacing the mat and putting a new surface line of the object inside the field of the camera 9 or 9A. The progression step is determined according to the definition chosen for the image. A linear resolution is preferably chosen in the order of 0.5 mm at the most by placing it in the field/of an optical and electronic unit having an angular resolution-close to 0.5 mrad at a distance of about 1 m. The mat 5 having progressed by one step, a synchronization element then generates from the clock signals a command signal for recording of the image by the recording system. Where the combination of an electronic camera and revolving mirror (FIG. 2) is used, the command signal is adapted to synchronize the rotation speed of the motor 11 and to trigger off acquisition of the image and its transformation into electrical signals. In the case of a camera used for recording by lines (FIG. 3), the command signal is adapted to trigger off the sequential reading of the various sensors of the sensitive terminal. In all cases, the indications of the counter with each progression step of the mat are transferred onto the corresponding recording which enables the image of any surface position of the object to be quickly retrieved. On can also arrange all along the object and on its sides a centrimetric scale enabling a determined area of the surface to be found very quickly.

The electrical signals derived from the optical and elelctronic unit are transmitted by a cable 15 to a microcomputer 16 which converts them into numeric words then transferred to a recording device 17, for example a tape recorder. The signals can also be transferred to a display device such as a TV monitor in such a way as to obtain a direct or different representation of the surface of the recorded object.

The microcomputer is also connected to a panel 19 enabling an operator to launch recording operations or to control special operations processing recorded data. The microcomputer is programmed, for example, to carry out processing in real time of data supplied by the camera before being recorded on the recording device 17, or in delayed time as regards pre-recorded data.

The camera can be connected to an optical filtering device allowing for selection of one or several bands over the whole width of the frequency specturm of the radiation received from the object, from ultraviolet to micro-waves (wave lengths between 30 nm and 30 cm). The visible spectral band enables sedimentary figures to be identified by the quantification of colours and their geometrical arrangement : lineaments, deformations, etc. The spectral band situated in the thermal infrared enables sedimentary groups to be differentiated according to their thermal inertia. The ultra-high frequencies enable information to be obtained concerning the fluid content of constituents and their granulometry or roughness.

The process according to the invention, when applied to the acquisition of images of geological cores, can be favourably implemented on the same extraction sites, on land, on a ship or an off-shore drilling platform. The cores, which have just been callipered and prepared by truncating and sawing following their axis, are arranged on the mobile table 1 prior to recording operations being carried out.

The process, even when the samples are no longer readily available for examination, enables a subsequent reproduction to be made of the images recorded for visual comparisons and consequently eliminates the need for the written codified descriptions previously required.

The process according to the invention is particularly useful in that it enables all sorts of systematic numeric processings to be made of recorded data. The elements can be classified according to their colours by referring to stored charts and, after simplification of the image by reduction to its contours, specialized pattern detection programs can be applied for identifying its components. The localization of discontinuities between layers enables calculation to be made of the spatial frequency of alterations and quantification of rhythms and sedimentary sequences. By means of a suitable programming applying known processes for calculating derivatives, the linear parts of each image can be isolated and it then becomes possible to distinguish the overring strata fracturing directions.

The computer-aided processing steps mentioned above are, for example, already used for the treatment of images taken from a plane or satellite.

These numeric processings can be applied to cores calliphered at spaced out intervals or from different sites. The large amount of data which can be obtained by these means and their objective characer facilitates correlation of samplings.

We claim:

1. A process for comparative optical analysis of configuration and geological nature of earth strata in a geological core taken out from penetrated underground formations, comprising the steps of: laying said geological core on a supporting means, step by step moving said supporting means nso as to pass said core in front of an opto-electronic system; forming successive images of parallel lines of a surface of said core on said opto-electronic system; convering said line images to electric digital signals; recording said signals; and comparing data read from said recorded signals fo line images of said geological core to corresponding data from signals of line images of other geological core surfaces previously recorded, whereby geological characteristics of said penetrated underground formations are more easily classified.

2. A process according ot claim 1, wherein the steps of forming successive images of parallel lines of a surface of said core on said opto-electronic system and converting said line images to electric digital signals is effected withou integration of a parallel line image.

3. A process for comparative optical analysis of configuration and geological nature of earth strata in a geological core taken out from penetrated underground formations, comprising the steps of: laying said geological core on a supporting means; step by step moving said supporting means so as to pass said core in front of an opto-electronic system; forming successive images of parallel lines of a surface of said geological core on said opto-electronic system; selecting a least one spectral band in radiations emanating from said geological core; converting said line images in said selected spectral band to electric digitals signals, recording said signals; and comparing data from said recorded signals of line images of said geological core to corresponding data of line images of other geological core surfaces previously recorded, whereby geological characteristics of said penetrated underground formations are more easily classified.

4. A process according to claim 3, wherein the steps of forming successive images of parallel lines of a surface of said core on said opto-electronic system and converting said line images to electric digital signals is effected without integration of a parallel line image.

5. A process for comparative optical analysis of configuration and geological nature of earth strata in a geological core taken out from penetrated underground formations, comprising the steps of: laying said geological core on a supporting means; step by step moving said supporting meansn so as to pass said core in front of an opto-electronic system; forming successive images of parallel lines of a surface of said geological core on said opto-electronic system; converting said line images to electric digital signals; recording said signals; processing said recorded signals for enhancing predetermined geological characteristics of said core; comparing data resulting from said processing operation for said geological core with correspondingn data from signals of line images of other geological core surfaces previously recorded, whereby geological characteristics of penetrated underground formations are more easily classified.

6. A process according to claim 5, wherein said step of processing includes effecting digital processing, and said step of comparing includes comparing the data resulting from said digital processing operation with the corresponding data of the geological core surfaces.

7. A process according to claim 6, wherein the step of digital processing includes effecting a spectral filtering operation.

8. A process according to claim 5, wherein the steps of forming successive images of parallel lines of a surface of said core on said opto-electronic system and converting said line images to electric digital signalsis effected without integration of a parallel line image.

9. A device for comparative optical analysis of configuration and geological nature of earth strata in a geological core taken out of from penetrated underground formations, comprising: means for supporting an elongated geological coroe; motor means for incremental displacement of said core with respect to a recording system; said recordingsystem including opto-electronic means for successively forming images of parallel lines of a surface of said geological core, conversion means for converting said images to electric digital signals, recording means for recording said signals, processing means comprising means for obtaining from said recorded signals of line images geological core data representing geological characteristics of said core means for ascertaining positions of the different strata in said geological core and means for comparing said data with corresponding data from previously recorded signals of line images of other geological cores.

10. A device according to claim 9, wherein said optical means includes a reflecting mobile element for successively directing, by scanning, the images of all the points of each line of said geological core surface onto an electronic camera.

11. A device according to claim 9, wherein said opto-electronic means includes a charge-coupled device.

12. A device according to claim 9, wherein said opto-electronic means includes optical filtering means for selecting at least one electromagnetic spectral band in radiations received from said core.

13. A device according to claim 9, wherein said supporting means includes a mobile table for supporting said core, said motor means includes a step by step drive motor for said mobile table, and further comprising synchronization means for alternately controlling said drive motor and said recording system.

14. A device according to claim 9, wherein said processing means includes computer means for digitally processing the recorded digital signals and for comparing said data resulting from said digital processing with corresponding data from previously recorded signals of line images of other geological cores.

15. A device according to claim 9 wherein said opto-electronic means for successively forming images of parallel lines of a surface of said geological core and said conversion means for converting said images to electric digital signals forms an image of a parallel line and converts said image to an electric digital signal without effecting integration of said image.

* * * * *